United States Patent [19]

Press et al.

[11] Patent Number: 4,670,560
[45] Date of Patent: Jun. 2, 1987

[54] THIENOPYRIMIDINE-2,4-DIONE DERIVATIVES AND INTERMEDIATES THEREOF

[75] Inventors: Jeffery B. Press, Rocky Hill; Ronald K. Russell, Pennington, both of N.J.

[73] Assignee: Ortho Pharmaceutical Corporation, Raritan, N.J.

[21] Appl. No.: 856,558

[22] Filed: Apr. 28, 1986

[51] Int. Cl.$^4$ .................................................. C07D 521/00
[52] U.S. Cl. ........................................ 544/278; 544/250; 544/376; 544/379
[58] Field of Search ................................ 544/278, 250

[56] References Cited

U.S. PATENT DOCUMENTS

| | | | |
|---|---|---|---|
| 3,272,811 | 9/1966 | Ohnacker et al. | 544/278 |
| 4,146,716 | 3/1979 | Cox | 544/278 |
| 4,562,193 | 12/1985 | Yamamoto et al. | 544/278 |

*Primary Examiner*—Glennon H. Hollrah
*Assistant Examiner*—James H. Turnipseed
*Attorney, Agent, or Firm*—Benjamin F. Lambert

[57] ABSTRACT

The synthesis of thienopyrimidine-2,4-dione derivatives and their urea intermediates is described. The novel urea intermediates and thienopyrimidine-2,4-dione derivatives are generally vasodilating agents and antihypertensive agents. The compounds are useful as cardiovascular agents.

12 Claims, No Drawings

THIENOPYRIMIDINE-2,4-DIONE DERIVATIVES AND INTERMEDIATES THEREOF

BACKGROUND OF THE INVENTION

1. Field of the Invention

The present invention relates to novel thienopyrimidine-2,4-dione derivatives of general formula I:

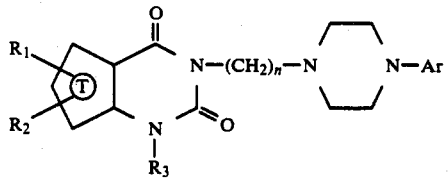

or their intermediates of general formula II:

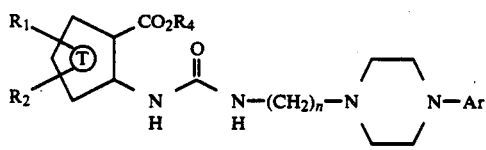

as described further below. The derivatives and intermediates are useful as cardiovascular agents, such as antihypertensive or general vasodilatng agents.

2. Description of the Prior Art

Several thienopyrimidine compounds have been previously described which have a variety of biological activities. For example, Chem. Abstr. 87, 201452 describes thienopyrimidine-2,4-dione compounds of the formula

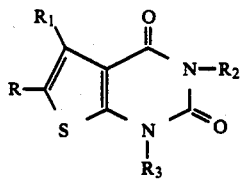

in which $R_2$ is methyl or phenyl and $R_3$ is acetylenic chains with amine termini. No utility was disclosed for these compounds.

Belgian Pat. No. 799238A describes thienopyrimidine-2-one compounds as CNS, uricosuric, antiviral or antiinflammatory agents. The compounds have the general formula

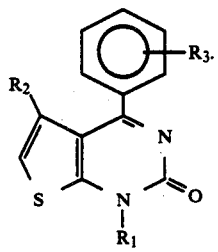

Belgain Pat. No. 796003 describes similar compounds having an additional substituent on the thiophene ring. The latter compounds have the same activity as the former compounds.

British Pat. No. 1,057612 describes several thienopyrimidine compounds having different activities such as fungistatic, bacteriostatic, cytostatic, antiphlogistic, CNS stimulating and cardiovascular activity. Compounds of the formula

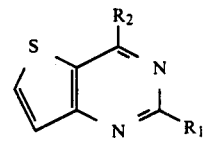

where $R_1$ or $R_2$ are N-methylpiperazine are said to have good cardiovascular effects. Additional compounds include those of the following general formulas:

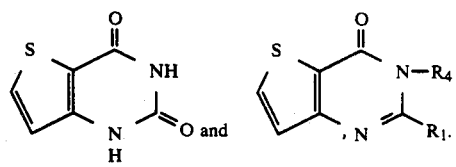

Derwent Accession No. 66-23,767/00 describes compounds of the formula

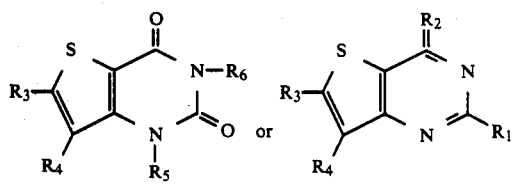

which have coronary or peripheral vasodilator activity as well as CNS activity. In the dione compounds, $R_5$ and $R_6$ may be alkyl or aryl.

Chem.Abs. 104, 19606q (EP 150469) describes thienopyrimidine compounds which are antidepressants and which have the formula:

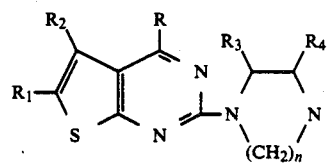

where R may be aryl or thieno and $R_1$ and $R_2$ may be hydrogen, alkyl, halo or alkylene.

Finally, H. K. Gaklar et al., Indian J. Chem. Sec. B, 24B, 432 (1985) describes the preparation of thienopyrimidine-4-ones having the formula:

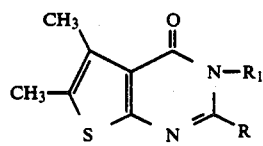

No biological activity was disclosed for these compounds.

None of the thienopyrimidine compounds of the prior art discussed above contain an N-alkyl-N-arylpiperazine moiety, i.e.,

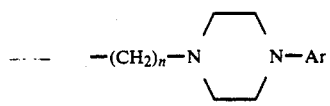

at the 3-position. Furthermore, several of the compounds are not diones and do not contain the same substituents at the 1-position of the present invention.

SUMMARY OF THE INVENTION

The present invention is directed to thienopyrimidine compounds of the formula

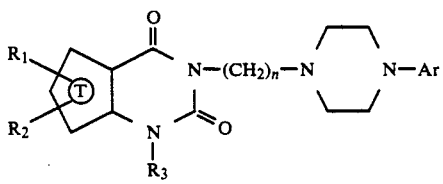                                    I where may be

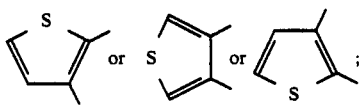

$R_1$ and $R_2$ may be the same or different and may be hydrogen, F, Cl, Br, nitro, $C_1$-$C_3$ alkyl or $R_1$ and $R_2$ together may be —$(CH_2)_4$— when

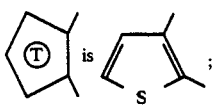

$R_3$ may be hydrogen, $C_1$-$C_{10}$ alkyl, $C_3$-$C_8$ branched-chain alkyl, $C_3$-$C_6$ alkenyl, $C_3$-$C_6$ alkynyl, —$(CH_2)_m$—$CO_2R_5$, —$(CH_2)_m CONR_6R_7$, —$COR_8$ or —$CO_2R_9$;

$R_5$ may be hydrogen, $C_1$-$C_3$ alkyl, pharmaceutically acceptable alkali metal ion, pharmaceutically acceptable alkaline earth metal ion or pharmaceutically acceptable quaternary ammonium ion;

$R_6$ and $R_7$ may be the same or different and may be hydrogen or $C_1$-$C_3$ alkyl;

$R_8$ may be $C_1$-$C_5$ alkyl, $C_3$-$C_5$ branched-chain alkyl, —$(CH_2)_m$—$CO_2R_5$, phenyl or phenyl substituted by F, Cl, Br, $C_1$-$C_2$ alkyl or $C_1$-$C_2$ alkoxy;

$R_9$ may be $C_1$-$C_3$ alkyl;

Ar may be

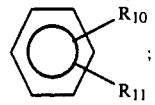

$R_{10}$ and $R_{11}$ may be the same or different and may be hydrogen, $NO_2$, $CF_3$, F, Cl, Br, $C_1$-$C_3$ alkyl or $C_1$-$C_2$ alkoxy;

m may be 2–6; and n may be 2–4.

The present invention is further directed to intermediates of the compounds of formula I having the formula

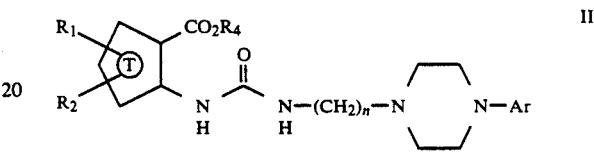                                    II where

$R_1$, $R_2$, Ar and n are as defined above and $R_4$ may be $C_1$-$C_2$ alkyl.

The compounds of formula I or II are useful as cardiovascular agents, such as antihypertensive agents or general vasodilating agents, especially renal vasodilating agents.

DETAILED DESCRIPTION OF THE INVENTION

The invention in its broadest aspects relates to thienopyrimidine-2,4-dione compounds and intermediates thereof which have cardiovascular activity, such as antihypertensive activity or general vasodilator activity, in mammals. The thienopyrimidine-2,4-dione compounds of the invention demonstrating a cardiovascular activity are shown by formula I above. The intermediates of these compounds which also have a cardiovascular activity are shown by formula II above. The thienopyrimidine-2,4-dione compounds and intermediates which have a cardiovascular activity all contain a nitrogen, either in the pyrimidine ring of the thienopyrimidine-2,4-diones or in the urea moiety of the intermediates, which is substituted by the group

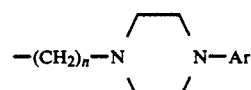

where n and Ar are as defined above.

The thienopyrimidine component of formula I may be either thieno[3,4-d]pyrimidine, thieno[2,3-d]pyrimidine or thieno[3,2-d]pyrimidine. The S atom in the intermediate compounds of formula II may occupy the equivalent position in the thiophene ring as it does in the thienopyrimidine compounds.

The preferred compounds of the present invention are those wherein $R_1$ is hydrogen or alkyl; $R_2$ is hydrogen or alkyl; $R_3$ is hydrogen, alkyl, branched-chain alkyl, alkenyl, alkynyl, —$(CH_2)_m$—$CO_2R_5$; —$COR_8$ or —$CO_2R_9$; $R_5$ is hydrogen or alkyl; $R_8$ is alkyl, branched-chain alkyl, —$(CH_2)_m$—$CO_2R_5$, phenyl or chlorophenyl; Ar is phenyl, chlorophenyl, fluorophenyl, methylphenyl or alkoxyphenyl; m is 2–4, and n is 2–3.

The compounds of formulas I and II can be prepared as shown in the following scheme.

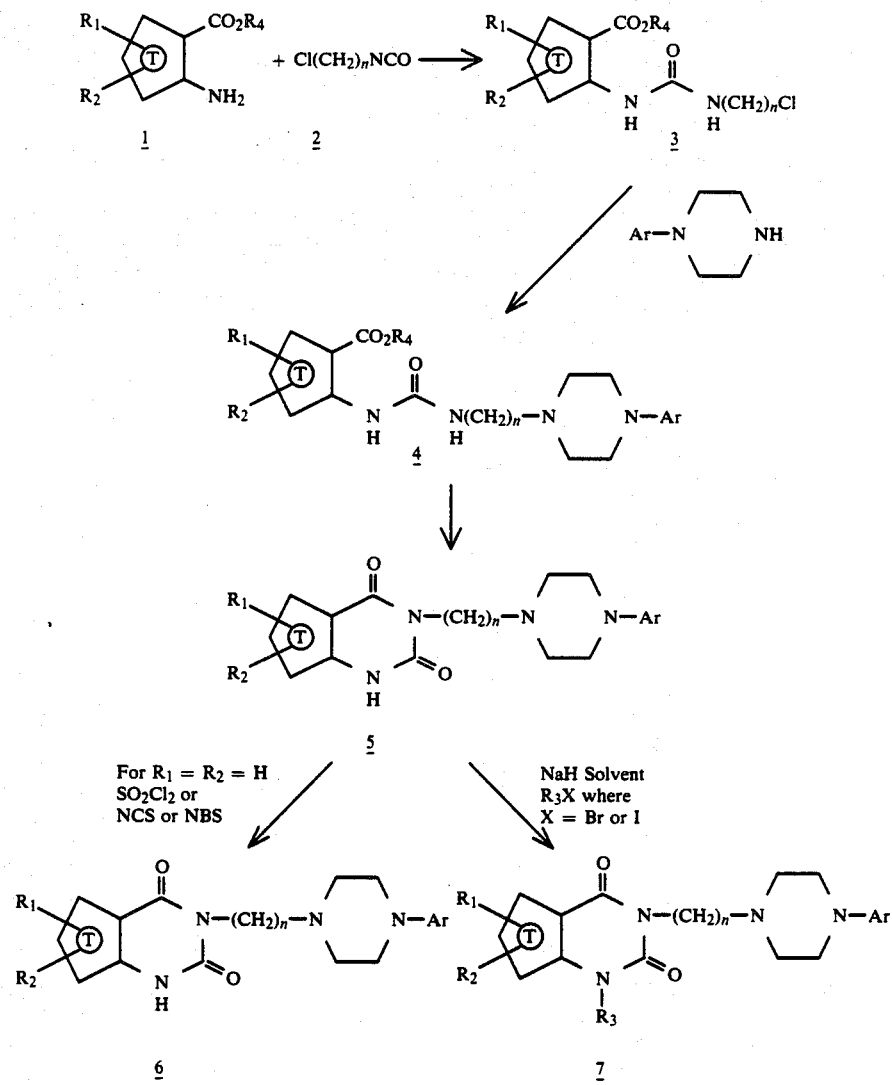

The compounds of formula II are prepared as follows:

An aminothiophene ester 1 is mixed with a chloroalkyl isocyanate 2 in an inert solvent at about 75° C. to about 115° C. about 1 to about 24 hours and the chloroalkyl urea 3 is produced as a white solid. The aminothiophene esters 1 are obtained commercially or prepared by the procedure of B. R. Baker, et al., *J. Org. Chem.* 18, 138 (1953). Suitable chloroalkyl isocyanates 2 include the 2-chloroethyl, 3-chloropropyl and 4-chlorobutyl isocyanates. The former two isocyanates are obtained commercially and the latter isocyanate is prepared according to S. Handa, et al., Ger. Offen. 2,622,194 (*Chem. Abst.* 86, 89372u (1977)). Inert solvents which may be utilized include toluene, tetrahydrofuran, dioxane and chloroform.

The crystalline chloroalkyl urea 3 is then reacted with an N-arylpiperazine, where the aryl group (Ar) is as defined above, in an inert solvent at about 60° C. to about 80° C. for about 1 to about 4 days in the presence of an alkali metal base and a catalyst to produce the alkylpiperazine urea 4. Suitable inert solvents for this step include tetrahydrofuran, dioxane, dimethylformamide, acetonitrile and isopropanol. A preferred base is sodium or potassium bicarbonate and the preferred catalyst is sodium or potassium iodide. The alkylpiperazine urea 4 is isolated as a solid.

The compounds of formula I are prepared as follows:
An alkylpiperazine urea 4 is prepared as described above. The urea 4 can be isolated and converted to a thienopyrimidine-2,4-dione 5 or it can be converted directly. The conversion is accomplished in an alcoholic solvent which contains an alkali metal base at about 25° C. to about 65° C. for about ½ hour to about 24 hours. Suitale alcohols include methanol, ethanol and isopropanol. Preferred alkali metal bases include sodium or potassium hydroxide or sodium hydride. The resulting novel thienopyrimidine-2,4-dione 5 is obtained as a solid.

The dione 5 can be alkylated at the 1-position by treatment in an inert solvent with an alkali metal base and subsequent treatment with an alkyl halide, $R_3X$, at about 5° C. to about 25° C. for about 1½ to about 16 hours to produce the alkylated derivative 7 as a white crystalline solid. Suitable inert solvents include tetrahydrofuran, dimethoxyethane and dimethylformamide. The preferred alkali metal base is sodium hydride. Alkyl halides which can be used are commericially available and include those wherein the alkyl group is methyl, ethyl, isopropyl, decyl, 3-(methoxycarbonyl)propyl, 6-(ethoxycarbonyl)hexyl, allyl and propargyl, among others. The halide may be bromide or iodide.

The carboxylic acid derivative of 7, i.e., $R_3$ is $-(CH_2)_mCO_2H$, can be prepared by dissolving the carboxylic ester derivative of 7, i.e., $R_3$ is $-(CH_2)_mCO_2R_5$ where $R_5$ is a lower alkyl (prepared as in the preceding paragraph), in an aqueous alcoholic solvent and treating with an alkali metal base at about 25° C. for about 3 to about 24 hours. The carboxylic acid derivative is a white solid after neutralization. Suitable alcohols include methanol and ethanol. Preferred bases are sodium hydroxide and potassium hydroxide.

The carboxylic acids may be converted to their corresponding pharmaceutically acceptable salts by dissolving the acids in an alcoholic solvent, for example methanol or ethanol, and treating them with an appropriate base. Appropriate bases include sodium hydroxide, potassium hydroxide, calcium hydroxide, triethylamine, tetrabutylammonium hydroxide and the like. The salts are obtained as solids after removal of the solvent.

The carboxylic ester derivative of 7, i.e., $R_3$ is $-(CH_2)_mCO_2R_5$, can be converted to the corresponding amides, i.e., $R_3$ is $-(CH_2)_mCONR_6R_7$, by standard condensation procedures or by the method of S. Weinreb, et al., *Tetrahedron Letters*, 4174 (1977). In the latter method, the ester is added to an inert solvent, such as methylene chloride, containing trimethylaluminum and an amine at about 25° C. to about 41° C. for about 5 to about 45 hours. Suitable amines include ammonia, methylamine, dimethylamine or propylamine and the like. The amides are isolated as solids.

The dione 5 can be acylated at the 1-position by refluxing the dione 5 with an acylating agent, such as acetic anhydride or benzoic anhydride, for about 1 to about 24 hours. Alternatively, the acylated derivative 7 can be prepared by treating the dione 5 with a strong base and an acid chloride in a polar solvent. The preferred strong bases are sodium hydride or lithium diisopropylamide. Suitable polar solvents include tetrahydrofuran, dimethyl sulfoxide, dimethylformamide and N-methylpyrrolidone. Acid chlorides include acetyl chloride, trimethylacetyl chloride, benzoyl chloride and the like. A final approach is to treat the dione 5 with an amine base such as triethylamine and an acid chloride in a solvent such as methylene chloride or chloroform.

The dione 5 can be halogenated by dissolving it in an inert solvent, such as methylene chloride or chloroform, and treating it with a halogenating agent to produce the halogen derivative 6. Suitable halogenating agents include sulfuryl chloride, N-chlorosuccinimide, N-bromosuccinimide, bromine and the like. Alternatively, the halogen derivatives 6 can be prepared by treating the urea 3 in the same manner and then reacting the halogenated urea 3 with the N-arylpiperazine.

The nitro derivative 7 can be prepared in a similar fashion by treating either the dione 5 or urea 3 with nitric acid in acetic anhydride or similar nitrating conditions. The nitrated urea 3 is then reacted with the N-arylpiperazine and reacted as above to give 5.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally contain dosage unit, e.g., tablet, capsule, powder, injection, teaspoonful and the like, from about 0.5 to about 100 mg/kg, and preferably from about 1 to about 5 mg/kg of the active ingredient.

The following examples describe the invention in greater particularity and are intended to be a way of illustrating but not limiting the invention.

EXAMPLE 1

3-[2-[4-(2-Methoxyphenyl)piperazin-1-yl]ethyl]-thieno[3,4-d]pyrimidine-2,4-dione (a) An aqueous solution of 9.65 g (50 mmol) of methyl 4-amino-3-thiophenecarboxylate hydrochloride (B. R. Baker, et al., *J. Org. Chem.*, 18, 138 (1953)) was treated with a saturated $NaHCO_3$ solution and then extracted with $CH_2Cl_2$. After drying the $CH_2Cl_2$ extracts over $MgSO_4$, the organic solution was evaporated to give the amine free base. This material was dissolved in 100 ml of toluene and treated with 4.7 ml (55 mmol) of 2-chloroethyl isocyanate. After this solution had been warmed to 100° C. for 3 hours, it was cooled and 7.9 g of N-(3-carbomethoxythien-4-yl)-N'-(2-chloroethyl)urea precipitated and was collected by filtration. The mother liquor afforded an additional 4.3 g (12.2 g total, 93%) of product which was recrystallized from $CH_2Cl_2$/ether/hexane (2/2/1), mp 110°–112° C.

Theor. $C_9H_{11}ClN_2O_3S$: C, 41.14; H, 4.22; N, 10.66. Found: C, 41.04; H, 4.17; N, 10.97.

The product produced in the preceding paragraph (5.2 g, 20 mmol) was dissolved in 60 ml of dry dimethylformamide and treated with 5.89 g (30 mmol) of 1-(2-methoxyphenyl)piperazine. After this solution had been warmed to 80° C. under nitrogen for 16 hours, it was cooled and 2.3 g of 1-(2-methoxyphenyl)piperzine hydrochloride was removed by filtration. The filtrate was concentrated in vacuo and the residue was purified by flash silica gel chromatography using 1-3% EtOH in $CH_2Cl_2$. The title compound was isolated and converted with isopropanolic hydrogen chloride to its hydrochloride salt (0.78 g, 9.2%), mp 270°-273° C. (dec.).

Theor. $C_{19}H_{22}N_4O_3S \cdot HCl$: C, 53.95; H, 5.48; N, 13.25. Found: C, 54.10; H, 5.59; N, 12.82.

(b) A 500 ml tetrahydrofuran mixture containing 13.1 g (50 mmol) of N-(3-carbomethoxythien-4-yl)-N'-(2-chloroethyl)urea from (a), 35 g (150 mmol) of 1-(2-methoxyphenyl)piperazine hydrochloride, 21 g (250 mmol) of sodium bicarbonate and 3.75 g (25 mmol) of sodium iodide was heated to reflux under nitrogen for 4 days. The tetrahydrofuran was removed in vacuo and the residue was partitioned between $H_2O$ and $CH_2Cl_2$. The $CH_2Cl_2$ extracts were dried over $MgSO_4$ and evaporated to dryness. This residue which contained the title compound of Example 2 was dissolved in 300 ml of methanol and treated with 4.5 g (56 mmol) of 50% NaOH. After the solution had been stirred at room temperature for 16 hours, the resulting precipitate was collected by filtration to afford 9.7 g of the title compound. The filtrate was purified by flash silica gel chromatography using 1-5% MeOH in $CH_2Cl_2$. There was obtained an additional 3.4 g of the title compound (13.1 g total, 68%) which was converted to its hydrochloride salt with isopropanolic hydrogen chloride, 9.1 g, mp 273°-275° C. (dec).

EXAMPLE 2

N-(3-Carbomethoxythien-4-yl)-N'-[2-[4-(2-methoxyphenyl)piperazin-1-yl]ethyl]urea (a) The title compound was also produced by the procedure of Example 1(a). The silica gel chromatography described in the second paragraph afforded the title compound as a faster running component which was converted with isopropanolic hydrogen chloride to its dihydrochloride salt (1.1 g, 11%), mp 195°-199° C.

Theor. $C_{20}H_{26}N_4O_4S \cdot 2HCl$: C, 48.88; H, 5.74; N, 11.40. Found: C, 48.85; H, 5.73, N, 11.59.

(b) Prepared as described in Example 1(b).

EXAMPLE 3

3-[2-[4-(2-Methylphenyl)piperazin-1-yl]ethyl]thieno[3,4-d]pyrimidine-2,4-dione

The title compound was produced following the procedure of Example 1(b) using 1-(2-methylphenyl)piperazine hydrochloride (40 mmol). The title compound was isolated in 38% yield (2.85 g) after recrystallization from $EtOAc/CH_2Cl_2$, mp 214°-216° C.

Theor. $C_{19}H_{22}N_4O_2S$: C, 61.60; H, 5.99; N, 15.12. Found: C, 61.22; H, 6.10; N, 15.23.

EXAMPLE 4

3-[2-[4-(2-Chlorophenyl)piperazin-1yl]ethyl]thieno[3,4-d]pyrimidine-2,4-dione

The title compound was produced following the procedure of Example 1(b) using 1-(2-chlorophenyl)piperazine (40 mmol). The title compound was isolated in 39% yield (3.03 g) after recrystallization from EtOH/EtOAc (½), mp 205°-207° C. (dec).

Theor. $C_{18}H_{19}ClN_4O_2S$: C, 55.30; H, 4.90; N, 14.33. Found: C, 54.87; H, 5.03; N, 14.20.

EXAMPLE 5

3-[2-[4-(3-Chlorophenyl)piperazin-1-yl]ethyl]thieno[3,4-d]pyrimidine-2,4-dione

The title compound was produced following the procedure of Example 1(b) using 1-(3-chlorophenyl)piperazine hydrochloride (40 mmol). The title compound was isolated in 19% yield (1.5 g) after crystallization from MeOH/EtOAc, mp 207°-208° C.

Theor. $C_{18}H_{19}ClN_4O_2S$: C, 55.30; H, 4.90; N, 14.33. Found: C, 55,50; H, 4.98; N, 14.10.

EXAMPLE 6

3-[2-[4-(4-Methoxyphenyl)piperazin-1-yl]ethyl]thieno[3,4-d]pyrimidine-2,4-dione

The title compound was produced following the procedure of Example 1(b) using 1-(4-methoxyphenyl)piperazine hydrochloride (40 mmol). The title compound was isolated in 14.6% yield (1.13 g) after recrystallization from MeOH/ether, mp 238°-239° C.

Theor. $C_{19}H_{22}N_4O_3S$: C, 59.05; H, 5.74; N, 14.50. Found: C, 59.12; H, 5.81; N, 14.70.

EXAMPLE 7

3-[2-[4-(3-Methoxyphenyl)piperazin-1-yl]ethyl]thieno[3,4-d]pyrimidine-2,4-dione

The title compound was produced following the procedure of Example 1(b) using 1-(3-methoxyphenyl)piperazine dihydrochloride (40 mmol). The title compound was isolated in 18% yield (1.4 g) after recrystallization from EtOH/hexane, mp 184.5°-185.5° C.

Theor. $C_{19}H_{22}N_4O_3S$: C, 59.05; H, 5.74; N, 14.50. Found: C, 58.86; H, 5.85; N, 14.47.

EXAMPLE 8

3-[2-[4-(4-Chlorophenyl)piperazin-1-yl]ethyl]thieno[3,4-d]pyrimidine-2,4-dione

The title compound was produced following the procedure of Example 1(b) using 1-(4-chlorophenyl)piperazine dihydrochloride (40 mmol). The title compound was converted to its hydrochloride salt with isopropanolic hydrogen chloride and isolated in 26% yield (2.21 g), mp>250° C.

Theor. $C_{18}H_{19}ClN_4O_2S \cdot HCl$: C, 50.59; H, 4.72; N, 13.11. Found: C, 50.51; H, 4.80; N, 12.82.

EXAMPLE 9

3-[2-[4-(4-Fluorophenyl)piperazin-1-yl]ethyl]thieno[3,4-d]pyrimidine-2,4-dione

The title compound was produced following the procedure of Example 1(b) using 1-(4-fluorophenyl)piperazine (40 mmol). The title compound was converted to its hydrochloride salt with isopropanolic hydrogen chloride and isolated in 18% yield (1.46 g), mp>250° C.

Theor. $C_{18}H_{19}FN_4O_2S \cdot HCl$: C, 52.62; H, 4.66; N, 13.64. Found: C, 52.35; H, 4.86; N, 13.85.

EXAMPLE 10

3-[2-(4-Phenylpiperazin-1-yl)ethyl]thieno[3,4-d]pyrimidine-2,4-dione

The title compound was produced following the procedure of Example 1(b) using 1-phenylpiperazine (40 mmol). The title compound was converted to its hydrochloride salt with isopropanolic hydrogen chloride and isolated in 21% yield (1.62 g), mp>250° C.

Theor. $C_{18}H_{20}N_4O_2S\cdot HCl$: C, 55.03; H, 5.13; N, 14.26. Found: C, 55.31; H, 5.53; N, 14.29.

EXAMPLE 11

3-[3-[4-(2-Methoxyphenyl)piperazin-1-yl]propyl]-thieno[3,4-d]pyrimidine-2,4-dione The title compound was produced following the procedure of Example 1(b) using N-(3-carbomethoxy-thien-4-yl)-N'-(3-chloropropyl)urea as the intermediate urea (5.52 g, 20 mmol) which was produced according to the procedure in Example 1 (a) with the exception that the isocyanate used was 3-chloropropyl isocyanate (55 mmol). This new urea was afforded in 61% yield (8.5 g) and crystallized from ether/hexane, mp 80°–83° C.

Theor. $C_{10}H_{13}ClN_2O_3S$: C, 43.40; H, 4.74; N, 10.12. Found: C, 43.31; H, 4.80; N, 10.28.

The title compound was isolated in 56% yield (4.5 g) and was crystallized from EtOH, mp 187°–188.5° C.

Theor. $C_{20}H_{24}N_4O_3S$: C, 59.98; H, 6.04; N, 13.99. Found: C, 59.69; H, 6.04; N, 13.95.

EXAMPLE 12

3-[2-[4-(2-Methoxyphenyl)piperazin-1-yl]ethyl]-5-methylthieno[3,4-d]pyrimidine-2,4-dione The title compound was produced following the procedure of Example 1(b) using N-(3-carbomethoxy-4-methylthien-4-yl)-N'-(2-chloroethyl)urea as the intermediate urea (5.52 g, 20 mmol) which was produced according to the procedure in Example 1(a) with the exception that the thiophene used was methyl 4-amino-2-methyl-3-thiophenecarboxylate hydrochloride (10.4 g, 50 mmol) which was prepared by the method of D. Binder et al. (*Arch. Pharm.* (Weinheim, Ger.), 314(6), 557 (1981)). The title compound was converted to its hydrochloride salt with isopropanolic hydrogen chloride and isolated in 46% yield (4.0 g), mp 265°–267° C. (dec).

Theor. $C_{20}H_{24}N_4O_3S\cdot HCl$: C, 54.97; H, 5.77; N, 12.82. Found: C, 54.58; H, 5.88; N, 12.85.

When in the above procedure, methyl 4-amino-5-methyl-3-thiophenecarboxylate hydrochloride, methyl 4-amino-2,5-diethyl-3-thiophenecarboxylate hydrochloride, methyl 4-amino-2-nitro-3-thiophenecarboxylate hydrochloride or methyl 4-amino-2-propyl-3-thiophenecarboxylate hydrochloride is employed, the corresponding 7-methyl, 5,7-diethyl, 5-nitro or 5-propyl derivative is obtained.

EXAMPLE 13

3-[2-[4-(2-Methoxyphenyl)piperazin-1-yl]ethyl]-1-methylthieno[3,4-d]pyrimidine-2,4-dione To a 50 ml tetrahydrofuran solution of 1.5 g (3.88 mmol) of the product of Example 1(a) (as its free base) under nitrogen was added 0.2 g (5.82 mmol) of 60% NaH. After stirring at room temperature for 30 minutes, the orange solution was treated with 0.24 ml (3.88 mmol) of methyl iodide. The reaction was quenched with $H_2O$ after 16 hours and the tetrahydrofuran was removed by evaporation at reduced pressure. The tan residue was crystallized from $CH_2Cl_2$/ether (1:1) to afford the title compound in 41% yield (0.64 g), mp 167°–167.5° C.

Theor. $C_{20}H_{24}N_4O_3S\cdot\frac{1}{4}H_2O$: C, 59.31; H, 6.10; N, 13.84. Found: C, 59.48; H, 6.25; N, 13.64.

When in the above procedure, pentyl iodide, decyl iodide or 1-bromo-2-methylpropane is employed as the alkylating agent, the corresponding 1-pentyl, 1-decyl or 1-(2-methyl-propyl) derivative is obtained.

EXAMPLE 14

3-[2-[4-(2-Methoxyphenyl)piperazin-1-yl]ethyl]-1-(propen-3-yl)thieno[3,4-d]pyrimidine-2,4-dione The title compound was produced following the procedure of Example 13 using dimethylformamide as the solvent and allyl bromide (4.4 mmol) as the alkylating agent. The crude product was purified by flash silica gel chromatography using EtOAc/hexane (40/60). The title compound was isolated in 56% yield (0.96 g) after recrystallization from $CH_2Cl_2$/hexane, mp 131°–132° C.

Theor. $C_{22}H_{26}N_4O_3S$: C, 61.95; H, 6.14; N, 13.14. Found: C, 61.83; H, 6.24; N, 13.04.

When in the above procedure, 4-bromo-1-butene or 6-bromo-1-hexene is employed as the alkylating agent, the corresponding 1-(buten-4-yl) or 1-(hexen-6-yl) derivative is obtained.

EXAMPLE 15

3-[2-[4-(2-Methoxyphenyl)piperazin-1-yl]ethyl]-1-(propyn-3-yl)thieno[3,4-d]pyrimidine-2,4-dione The title compound was produced following the procedure of Example 13 using dimethylformamide as the solvent and propargyl bromide (4.4 mmol) as the alkylating agent. The crude product was purified by flash silica gel chromatography using EtOAc/hexane (1:1). The title compound was isolated in 49% yield (0.84 g) after recrystallization from ether/hexane, mp 142°–143° C.

Theor. $C_{22}H_{24}N_4O_3S$: C, 62.24; H, 5.70; N, 13.20. Found: C, 61.99; H, 5.83; N, 13.28.

EXAMPLE 16

3-[2-[4-(2-Methoxyphenyl)piperazin-1-yl]ethyl]-1-(octyl)thieno[3,4-d]pyrimidine-2,4-dione The title compound was produced following the procedure of Example 13 using dimethylformamide as the solvent and octyl bromide (12 mmol) as the alkylating agent. The crude product was purified by flash silica gel chromatography using EtOAc/hexane (1:1). The title compound was isolated in 47% yield (0.94 g) after recrystallization from ether/hexane, mp 82°–84° C.

Theor. $C_{27}H_{38}N_4O_3S$: C, 65.03; H, 7.68; N, 11.24. Found: C, 65.26; H, 7.73; N, 11.35.

EXAMPLE 17

1-(2-Methoxycarbonyl)ethyl-3-[2-[4-(2-methoxyphenyl)piperazin-1-yl]ethyl]thieno[3,4-d]pyrimidine-2,4-dione The title compound was produced following the procedure of Example 13 using dimethylformamide as the solvent and methyl 3-bromopropionate (4.4 mmol) as the alkylating agent. The crude product was purified by flash silica gel chromatography using 50–70% EtOAc in hexane. The title compound was isolated in 47% (0.89 g) yield after recrystallization from ether, mp 140°–140.5° C.

Theor. $C_{23}H_{28}N_4O_5S$: C, 58.45; H, 5.97; N, 11.86. Found: C, 58.21; H, 6.08; N, 11.89.

When the above product is treated with ammonia in accordance with Weinreb et al., vide supra, the corresponding 1-(3-propanamide)derivative is obtained.

EXAMPLE 18

1-[3-(Ethoxycarbonyl)propyl]-3-[2-[4-(2-methoxyphenyl)piperazin-1-yl]ethyl]thieno[3,4-d]pyrimidine-2,4-dione The title compound was produced following the procedure of Example 13 using dimethylformamide as the solvent and ethyl 4-bromobutyrate (3.9 mmol) as the alkylating agent. The title compound was produced in 65% yield (0.85 g) after recrystallization from ether, mp 108°–109.5° C.

Theor. $C_{25}H_{32}N_4O_5S$: C, 59.98; H, 6.44; N, 11.19. Found: C, 60.08; H, 6.47; N, 11.27.

EXAMPLE 19

3-[2-[4-(2-Methoxyphenyl)piperazin-1-yl]ethyl]thieno[3,2-d]pyrimidine-2,4-dione

The title compound was produced from N-(2-carbomethoxythien-3-yl)-N'-(2-chloroethyl)urea which was prepared in the same manner as described for N-(3-carbomethoxythien-4-yl)-N'-(2-chloroethyl)urea in Example 1(a) with the exception that the thiophene was methyl 3-amino-2-thiophenecarboxylate (28.3 g, 0.18 mol). This new urea was obtained in 56% yield (26.6 g) isolated from the reaction as a crystalline solid, mp 139°–142° C.

Theor. $C_9H_{11}ClN_2O_3S$: C, 41.15; H, 4.22; N, 10.66. Found: C, 41.30; H, 4.22; N, 10.68.

The product produced in the preceding paragraph (8.44 g, 32.1 mmol) was dissolved in 200 ml of tetrahydrofuran and treated with 14.68 g (64.2 mmol) of 1-(2-methoxyphenyl)piperazine hydrochloride, 8.12 g (96.6 mmol) of sodium bicarbonate and 1.7 g of sodium iodide. After the mixture had been refluxed for 2.5 days, the tetrahydrofuran was removed in vacuo and the residue was partitioned between $H_2O$ and $CH_2Cl_2$. The combined $CH_2Cl_2$ extracts were dried over $MgSO_4$ and concentrated in vacuo to afford a residue that was purified by flash silica gel chromatography using 2% MeOH in $CH_2Cl_2$. The urea, N-(2-carbomethoxythien-3-yl)-N'-[2-[4-[2-methoxyphenyl)piperazin-1-yl)ethyl]urea, was obtained in 67% yield (9.0 g), mp 149°–151° C.

Theor. $C_{20}H_{26}N_4O_4S$: C, 57.39; H, 6.26; N, 13.39. Found: C, 57.05; H, 6.27; N, 13.51.

A solution of this intermediate (7.0 g, 16.7 mmol) in 50 ml 1N methanolic KOH was refluxed for 1 hour, poured into 200 ml of ice water and neutralized. The title compound was isolated in 72% yield (4.65 g) after trituration with hot ethanol, mp 222°–223° C.

Theor. $C_{19}H_{22}N_4O_3S \cdot \frac{1}{4}H_2O$: C, 58.37; H, 5.80; N, 14.33. Found: C, 58.56; H, 5.79; N, 14.26.

EXAMPLE 20

3-[2-[4-(2-Methylphenyl)piperazin-1-yl]ethyl]thieno[3,2-d]pyrimidine-2,4-dione

The title compound was produced following the procedure of Example 19 using 1-(2-methylphenyl)piperazine hydrochloride (22.8 mmol) and an initial reflux period of 4 days. The intermediate urea, N-(2-carbomethoxythien-3-yl)-N'-[2-[4-(2-methylphenyl)piperazin-1-yl]ethyl]urea, was isolated in 48% yield (2.2 g), mp 118°–123° C.

The product from the preceding paragraph (2.1 g, 5.2 mmol) was converted to the title compound as described in Example 19 in 73% yield (1.4 g) after it had been triturated in boiling ethanol, mp 212°–214° C.

Theor. $C_{19}H_{22}N_4O_2S$: C, 61.60; H, 5.99; N, 15.12. Found: C, 61.74; H, 6.26; N, 14.99.

EXAMPLE 21

3-[2-[4-(2-Chlorophenyl)piperazin-1-yl]ethyl]thieno[3,2-d]pyrimidine-2,4-dione

The title compound was produced following the procedure of Example 19 using 1-(2-chlorophenyl)piperazine hydrochloride (22.8 mmol) and an initial reflux period of 4 days. The intermediate urea, N-(2-carbomethoxythien-3-yl)-N'-[2-[4-(2-chlorophenyl)piperazin-1-yl]ethyl]urea, was isolated in 59% yield (2.88 g), mp 61°–65° C.

The product from the preceding paragraph (2.8 g, 6.62 mmol) was converted to the title compound in 77% yield (1.99 g), mp 193°–196° C., using the procedure in Example 19.

Theor. $C_{18}H_{19}ClN_4O_2S$: C, 55.31; H, 4.90; N, 14.35. Found: C, 54.95; H, 4,93; N, 14.12.

EXAMPLE 22

3-[2-[4-(4-Methoxyphenyl)piperazin-1-yl]ethyl]thieno[3,2-d]pyrimidine-2,4-dione

The title compound was produced following the procedure of Example 19 using 1-(4-methoxyphenyl)piperazine hydrochloride (22.8 mmol). The intermediate urea, N-(2-carbomethoxythien-3-yl)-N'-[2-[4-(4-methoxyphenyl)piperazin-1-yl]ethyl]urea, was isolated in 34% yield (1.6 g), mp 158°–160° C.

Theor. $C_{20}H_{26}N_4O_4S$: C, 57.29; H, 6.26; N, 13.39. Found: C, 57.29; H, 6.35; N, 13.30.

The product from the preceding paragraph (1.6 g, 3.86 mmol) was converted to the title compound in 80% yield (1.2 g), mp 130°–131° C., using the procedure in Example 19.

Theor. $C_{19}H_{22}N_4O_3S$: C, 59.05; H, 5.74; N, 14.50. Found: C, 58.87; H, 5.85; N, 14.37. When in the above procedure, methyl 3-amino-5-methyl-2-thiophenecarboxylate hydrochloride, methyl 3-amino-4-methyl-2-thiophenecarboxylate hydrochloride, methyl 3-amino-4,5-diethyl-2-thiophenecarboxylate hydrochloride, methyl 3-amino-5-nitro-2-thiophenecarboxylate hydrochloride or methyl 3-amino-5-propyl-2-thiophenecarboxylate hydrochloride is employed, the corresponding 5-methyl, 7-methyl, 5,7-diethyl, 5-nitro or 5-propyl derivative is obtained.

EXAMPLE 23

3-[2-(4-Phenylpiperazin-1-yl)ethyl]thieno[3,2-d]pyrimidine-2,4-dione

The title compound was produced following the procedure of Example 19 using 1-phenylpiperazine (28.5 mmol) and an initial reflux period of 4 days. The intermediate urea, N-(2-carbomethoxythien-3-yl)-N'-[2-(4-phenylpiperazin-1-yl)ethyl]urea, was isolated in 57% yield (2.1 g), mp 162°–164° C.

Theor. $C_{19}H_{24}N_4O_3S$: C, 58.74; H, 6.23; N, 14.42. Found: C, 58.31; H, 6.03; N, 14.21.

The product from the preceding paragraph (2.1 g, 5.4 mmol) was converted to the title compound in 62% yield (1.2 g), mp 215°–217° C., using the procedure in Example 19.

Theor. $C_{18}H_{20}N_4O_2S$: C, 60.65; H, 5.66; N, 15.72. Found: C, 60.84; H, 5.65; N, 15.66.

EXAMPLE 24

3-[3-[4-(2-Methoxyphenyl)piperazin-1-yl]propyl]-thieno[3,2-d]pyrimidine-2,4-dione The title compound was produced following the procedure of Example 19 with the exception that the initial urea, N-(2-carbomethoxythien-3-yl)-N'-(3-chloropropyl)urea, was produced according to the procedure in Example 19 except that the isocyanate used was 3-chloropropyl isocyanate (76 mmol) and the reflux period was 2.5 days. This chloropropyl urea was crystallized from hexanes in 61% yield (10.6 g), mp 78°–84° C.

Theor. $C_{10}H_{13}ClN_2O_3S$: C, 43.40; H, 4.73; N, 10.12. Found: C, 43.21; H, 4.62; N, 10.02.

The product from the preceding paragraph (5.0 g, 19.2 mmol) was converted to the intermediate urea, N-(2-carbomethoxythien-3-yl)-N'-[3-[4-(2-methoxyphenyl)piperazin-1-yl]propyl]urea, using the procedure in Example 19 in 79% yield (6.4 g), mp 149°–151° C.

Theor. $C_{21}H_{28}N_4O_4S$: C, 58.31; H, 6.52; N, 12.95. Found: C, 57.92; H, 6.57; N, 12.86.

The product from the preceding paragraph (6.4 g, 15.2 mmol) was converted to the title compound in 52% yield (3.15 g), mp 205°–206° C., using the procedure in Example 19.

Theor. $C_{20}H_{24}N_4O_3S \cdot \frac{1}{4}H_2O$: C, 59.31; H, 6.10; N, 13.83. Found: C, 59.38; H, 6.00; N, 13.80.

EXAMPLE 25

3-[2-[4-(2-Methoxyphenyl)piperazin-1-yl]ethyl]-1-methylthieno[3,2-d]pyrimidine-2,4-dione The title compound was produced following the procedure of Example 13 using dimethylformamide as the solvent and the thienopyrimidine-2,4-dione (1.82 g, 4.66 mmol) from Example 19. The title compound was isolated in 61% yield (1.13 g) after recrystallization from EtOH, mp 149°–151° C.

Theor. $C_{20}H_{24}N_4O_3S$: C, 59.98; H, 6.04; N, 13.90. Found: C, 59.70; H, 5.82; N, 13.95.

When in the above procedure, pentyl iodide, decyl iodide or 1-bromo-2-methylpropane are employed as the alkylating agent, the corresponding 1-pentyl, 1-decyl or 1-(2-methyl-propyl) derivative is obtained.

EXAMPLE 26

1-(Butyl)-3-[2-[4-(2-methoxyphenyl)piperazin-1-yl]ethyl]thieno[3,2-d]pyrimidine-2,4-dione The title compound was produced following the procedure of Example 13 using dimethylformamide as the solvent, the thienopyrimidine-2,4-dione (2.0 g, 5.17 mmol) from Example 19, and butyl iodide as the alkylating agent. The title compound was isolated in 56% yield (1.28 g) after recrystallization from EtOH, mp 139°–140° C.

Theor. $C_{23}H_{30}N_4O_3S$: C, 62.42; H, 6.83; N, 12.66. Found: C, 62.57; H, 6.90; N, 12.68.

When in the above procedure, allyl bromide, 4-bromo-1-butene, 6-bromo-1-hexene, propargyl bromide or methyl 3-bromopropionate is employed as the alkylating agent, the corresponding 1-(propen-3-yl), 1-(buten-4-yl), 1-(hexen-6-yl), 1-(propyn-3-yl) or 1-((2-methoxycarbonyl)ethyl) derivative is obtained.

EXAMPLE 27

1-[4-(Ethoxycarbonyl)butyl]-3-[2-[4-(2-methoxyphenyl)piperazin-1-yl]ethyl]thieno[3,2-d]pyrimidine-2,4-dione The title compound was produced following the procedure of Example 13 using dimethylformamide as solvent, the thienopyrimidine-2,4-dione (3.0 g, 7.76 mmol) from Example 19, and ethyl 5-bromovalerate was used as the alkylating agent. The title compound was isolated in 82% yield (3.3 g), after recrystallization from EtOH, mp 118°–119° C.

Theor. $C_{26}H_{34}N_4O_5S$: C, 60.68; H, 6.66; N, 10.87. Found: C, 60.72; H, 6.67; N, 10.83.

When the above product is treated with ammonia in accordance with Weinreb et al., vide supra, the corresponding 1-(4-butyramide) derivative is obtained.

EXAMPLE 28

3-[2-[4-(2-Methoxyphenyl)piperazin-1-yl]ethyl]-thieno[2,3-d]pyrimidine-2,4-dione The title compound was produced from N-(3-carboethoxythien-2-yl)-N'-(2-chloroethyl)urea which was prepared in the same fashion as described for N-(3-carbomethoxythien-4-yl)-N'-(2-chloroethyl)urea in Example 1(a) except that the thiophene was ethyl 2-amino-3-thiophenecarboxylate (9.5 g, 55.5 mmol) and the reflux time was 16 hours. This new urea was isolated in 44% yield (6.7 g) by flash silica gel chromatography using 12.5% EtOAc in hexanes, mp 85°–87° C.

Theor. $C_{10}H_{13}ClN_2O_3S$: C, 43.40; H, 4.73; N, 10.12. Found: C, 43.25; H, 4.83; N, 9.97.

The product (6 g, 21.7 mmol) from the preceding paragraph was converted to N-(3-carboethoxythien-2-yl)-N'-[2-[4-(2-methoxyphenyl)piperazin-1-yl]ethyl]urea using the procedure in Example 19. This intermediate urea was isolated on 74% yield (6.99 g) with mp 129°–132° C.

Theor. $C_{21}H_{28}N_4O_4S$: C, 58.31; H, 6.52; N, 12.95. Found: C, 58.50; H, 6.81; N, 12.85.

The title compound was produced from the product (6.0 g, 13.9 mmol) above in 78% yield (4.18 g), mp 234°–236° C., using the procedure in Example 19.

Theor. $C_{19}H_{22}N_4O_3S$: C, 58.80; H, 5.80; N, 14.76. Found: C, 59.05; H, 5.74; N, 14.50.

EXAMPLE 29

3-[2-[4-(2-Methylphenyl)piperazin-1-yl]ethyl]-thieno[2,3-d]pyrimidine-2,4-dione

The title compound was produced following the procedure of Example 19 using 1-(2-methylphenyl)piperazine hydrochloride and the chloroethyl urea (4.0 g, 14.4 mmol) described in Example 28. The intermediate urea, N-(3-carboethoxythien-2-yl)-N'-[2-[4-(2-methylphenyl)piperazin-1-yl]ethyl]urea, was isolated in 53% yield (3.2 g), mp 118°–123° C.

Theor. $C_{21}H_{28}N_4O_3S$: C, 60.55; H, 6.78; N, 13.45. Found: C, 60.37; H, 6.95; N, 13.38.

The product from the preceding paragraph (3.2 g, 7.68 mmol) was converted to the title compound in 89% yield (2.5 g) after recrystallization from EtOH, mp 191°–193° C., using the procedure in Example 19.

Theor. $C_{19}H_{22}N_4O_2S$: C, 61.60; H, 5.99; N, 15.12. Found: C, 61.35; H, 6.21; N, 14.98.

EXAMPLE 30

3-[2-[4-(2-Chlorophenyl)piperazin-1-yl]ethyl]-thieno[2,3-d]pyrimidine-2,4-dione

The title compound was produced according to the procedure of Example 19 using 1-(2-chlorophenyl)piperazine hydrochloride, the chloroethyl urea (4.0 g, 14.4 mmol) described in Example 28 and an initial reflux time of 4 days. The intermediate urea, N-(3-carbomethoxythien-2-yl)-N'-[2-[4-(2-chlorophenyl)piperazin-1-yl]ethyl]urea, was isolated in 81% yield (5.1 g), mp 141°–143° C.

Theor. $C_{20}H_{25}ClN_4O_3S$: C, 54.98; H, 5.77; N, 12.82. Found: C, 55.21; H, 6.07; N, 12.85.

The product from the preceding paragraph (5.0 g, 11.4 mmol) was converted to the title compound in 85% yield (3.77 g) after trituration with hot EtOH, mp 216°–217° C., using the procedure in Example 19.

Theor. $C_{18}H_{19}ClN_4O_2S$: C, 55.31; H, 4.90; N, 14.33. Found: C, 55.31; H, 4.95; N, 14.24.

EXAMPLE 31

3-[2-(4-Phenylpiperazin-1-yl)ethyl]thieno[2,3-d]pyrimidine-2,4-dione

The title compound was produced following the procedure of Example 19 using 1-phenylpiperazine, the chloroethyl urea (2.5 g, 9.03 mmol) described in Example 28, and an initial reflux period of 4 days. The intermediate, N-(3-carboethoxythien-2-yl)-N'-[2-(4-phenylpiperazin-1-yl)ethyl]urea, was isolated in 85% yield (3.1 g), mp 117°–120° C.

Theor. $C_{20}H_{26}N_4O_3S$: C, 59.68; H, 6.51; N, 13.92. Found: C, 59.72; H, 6.73; N, 13.83.

The product from the preceding paragraph (3.1 g, 7.7 mmol) was converted to the title compound in 89% yield (2.43 g) after trituration with hot ethanol, mp 228°–230° C., using the procedure in Example 19.

Theor. $C_{18}H_{20}N_4O_2S$: C, 60.65; H, 5.66; N, 15.72. Found: C, 60.64; H, 5.81; N, 15.62.

EXAMPLE 32

3-[2-[4-(4-Methoxyphenyl)piperazin-1-yl]ethyl]-thieno[2,3-d]pyrimidine-2,4-dione The title compound was produced following the procedure of Example 19 using 1-(4-methoxyphenyl)-piperazine hydrochloride, the chloroethyl urea (2.5 g, 9.03 mmol) described in Example 28, and an initial reflux period of 6 days. The intermediate, N-(3-carboethoxythien-2-yl)-N'-[2-[4-(4-methoxyphenyl)piperazin-1-yl]ethyl]urea, was isolated in 51% yield (2.0 g), mp 103°–106° C.

Theor. $C_{21}H_{28}N_4O_4S$: C, 58.31; H, 6.52; N, 12.95. Found: C, 58.01; H, 6.62; N, 12.89.

The product from the preceding paragraph (2.0 g, 4.62 mmol) was converted to the title compound in 97% yield (1.74 g) after trituration with hot EtOH, mp 249°–251° C., using the procedure in Example 19.

Theor. $C_{19}H_{22}N_4O_3S$: C, 59.05; H, 5.74; N, 14.50. Found: C, 58.81; H, 5.69; N, 14.40.

EXAMPLE 33

3-[3-[4-(2-Methoxyphenyl)piperazin-1-yl]propyl]-thieno[2,3-d]pyrimidine-2,4-dione The title compound was produced following the procedure of Example 19 using N-(3-carboethoxythien-2-yl)-N'-(3-chloropropyl) urea which was produced in the same fashion as that described in Example 24 except that the thiophene was ethyl 2-amino-3-thiophenecarboxylate (4.96 g, 29 mmol). This new urea was isolated in 51% yield (4.3 g) after flash silica gel chromatography using 15% EtOAc in hexane, mp 92°–95° C.

Theor. $C_{11}H_{15}ClN_2O_3S$: C, 45.44; H, 5.20; N, 9.63. Found: C, 45.84; H, 5.30; N, 9.38.

The product from the preceding paragraph (4.2 g, 14.4 mmol) was converted to the intermediate urea, N-(3-carboethoxythien-2-yl)-N'-[3-[4-(2-methoxyphenyl)piperazin-1-yl]propyl]urea, using the procedure in Example 19 in 64% yield (4.1 g), mp 43°–50° C.

Theor. $C_{22}H_{30}N_4O_4S$: C, 59.17; H, 6.77; N, 12.55. Found: C, 58.75; H, 7.16; N, 12.42.

The product from the preceding paragraph (4.0 g, 8.96 mmol) was converted to the title compound in 50% yield (1.8 g) after trituration with hot EtOH, mp 217°–218° C., using the procedure in Example 19.

Theor. $C_{20}H_{24}N_4O_3S$: C, 59.98; H, 6.04; N, 13.99. Found: C, 59.94; H, 6.13; N, 13.87.

EXAMPLE 34

3-[2-[4-(2-Methoxyphenyl)piperazin-1-yl]ethyl]-5-methylthieno[2,3-d]pyrimidine-2,4-dione The title compound was produced from N-(2-chloroethyl)-N'-(3-ethoxycarbonyl-4-methylthien-2-yl)urea which was prepared in the same fashion as described for N-(3-carbomethoxythien-4-yl)-N'-(2-chloroethyl)urea in Example 1(a) except that the thiophene was ethyl 2-amino-4-methyl-3-thiophenecarboxylate (18.5 g, 0.1 mol). This chloroethyl urea was isolated in 76% yield (22.3 g) and crystallized from $CH_2Cl_2$/ether (1:1), mp 126.5°–130° C.

Theor. $C_{11}H_{15}ClN_2O_3S$: C, 45.43; H, 5.20; N, 9.64. Found: C, 45.61; H, 5.39; N, 9.95.

The product from the preceding paragraph (5.8 g, 20 mmol) was converted to the title compound in 72% yield (5.8 g) following the procedure in Example 1(b), and this material was converted to its hydrochloride salt with isopropanolic hydrogen chloride, mp 209°–213° C.

Theor. $C_{20}H_{24}N_4O_3S.HCl.\frac{1}{2}H_2O$: C, 53.86; H, 5.88; N, 12.56. Found: C, 54.19; H, 5.89; N, 12.66.

When in the above procedure, methyl 2-amino-5-methyl-3-thiophenecarboxylate hydrochloride, methyl 2-amino-4,5-diethyl-3-thiophenecarboxylate hydrochloride, methyl 2-amino-5-nitro-3-thiophenecarboxylate hydrochloride or methyl 2-amino-5-propyl-3-thiophenecarboxylate hydrochloride is employed, the corresponding 7-methyl, 5,7-diethyl, 5-nitro or 5-propyl derivative is obtained.

EXAMPLE 35

6-Chloro-3-[2-[4-(2-Methoxyphenyl)piperazin-1-yl]ethyl]thieno[2,3-d]pyrimidine-2,4-dione The title compound was produced from N-(3-carboethoxy-5-chlorothien-2-yl)-N'-(2-chloroethyl)urea which was prepared by treating a 100 ml $CH_2Cl_2$ solution of the chloroethyl urea of Example 28 (5.0 g, 18.1 mmol) with 1.52 ml (19 mmol) of sulfuryl chloride at 0°–5° C. After the reaction mixture had been stirred at room temperature for 18 hours, the mixture was concentrated to 20 ml in vacuo and diluted with hexane. The intermediate urea was isolated in 84% (4.74 g) yield, mp 122°–128° C.

Theor. $C_{10}H_{12}Cl_2N_2O_3S$: C, 38.60; H, 3.89; N, 9.00. Found: C, 38.66; H, 4.07; N, 8.87.

The product from the preceding paragraph (4.7 g, 15.1 mmol) was converted to the intermediate urea, N-(3-carboethoxy-5-chlorothien-2-yl)-N'-[2-[4-(2-methoxyphenyl)piperazin-1-yl]ethyl]urea, using the procedure in Example 19 except that the reflux period was 3.5 days. This material was isolated in 86% yield (6.03 g), mp 53°-58° C.

Theor. $C_{21}H_{27}ClN_4O_4S$: C, 54.01; H, 5.82; N, 12.00. Found: C, 54.35; H, 6.28; N, 11.62.

The product from the preceding paragraph (6.0 g, 12.8 mmol) was converted to the title compound in 63% yield (3.42 g) after recrystallization from EtOH, mp 228°-230° C., using the procedure in Example 19.

Theor. $C_{19}H_{21}ClN_4O_3S$: C, 54.22; H, 5.03; N, 13.31. Found: C, 54.13; H, 5.20; N, 13.24.

EXAMPLE 36

3-[2-[4-(2-Methoxyphenyl)piperazin-1-yl]ethyl]-5,6-dimethylthieno[2,3-d]pyrimidine-2,4-dione The title compound was produced from N-(3-carboethoxy-4,5-dimethylthien-2-yl)-N'-(2-chloroethyl)urea, which was prepared in the same fashion as described for N-(3-carbomethoxythien-4-yl)-N'-(2-chloroethyl)urea in Example 1(a) except that the thiophene was ethyl 2-amino-4,5-dimethyl-3-thiophenecarboxylate (7.0 g, 35.1 mmol). This chloroethyl urea was isolated in 61% yield (6.5 g) after flash silica gel chromatography using 10% EtOAc in hexanes, mp 115°-116° C.

Theor. $C_{12}H_{17}ClN_2O_3S$: C, 47.29; H, 5.62; N, 9.19. Found: C, 47.25; H, 5.73; N, 9.14.

The product from the preceding paragraph (6.0 g, 21.7 mmol) was converted to the intermediate urea, N-(3-carboethoxy-4,5-dimethylthien-2-yl)-N'-[2-[4-(2-methoxyphenyl)piperazin-1-yl]ethyl]urea, in 89% yield (8.6 g), mp 56°-62° C., using the procedure in Example 19.

Theor. $C_{23}H_{32}N_4O_4S$: C, 59.98; H, 7.00; N, 12.16. Found: C, 59.60; H, 7.30; N, 11.80.

The product from the preceding paragraph (8.5 g, 18.5 mmol) was converted to the title compound in 85% yield (6.5 g) after trituration with hot EtOH, mp 196°-197° C., using the procedure in Example 19.

Theor. $C_{21}H_{26}N_4O_3S$: C, 60.85; H, 6.32; N, 13.52. Found: C, 60.70; H, 6.60; N, 13.48.

EXAMPLE 37

3-[2-[4-(2-Methoxyphenyl)piperazin-1-yl]ethyl]-1-methylthieno[2,3-d]pyrimidine-2,4-dione The title compound was produced following the procedure of Example 13 using dimethylformamide as the solvent and the thienopyrimidine-2,4-dione (2.0 g, 5.17 mmol) of Example 28. The title compound was isolated in 61% yield (1.13 g) after recrystallization from EtOH, mp 174°-176° C.

Theor. $C_{20}H_{24}N_4O_3S$: C, 59.98; H, 6.04; N, 13.99. Found: C, 60.04; H, 6.19; N, 14.03.

When in the above procedure, pentyl iodide, decyl iodide or 1-bromo-2-methylpropane is employed as the alkylating agent, the corresponding 1-pentyl, 1-decyl or 1-(2-methyl-propyl) derivative is obtained.

When in the above procedure, allyl bromide, 4-bromo-1-butene, 6-bromo-1-hexene, propargyl bromide or methyl 3-bromopropionate is employed as the alkylating agent, the corresponding 1-(propen-3-yl), 1-(buten-4-yl), 1-(hexen-6-yl), 1-(propyn-3-yl) or 1-((2-methoxycarbonyl)ethyl) derivative is obtained.

EXAMPLE 38

1-Acetyl-3-[2-[4-(2-methoxyphenyl)piperazin-1-yl]ethyl]thieno[3,4-d]pyrimidine-2,4-dione A solution of 3-[2-[4-(2-methoxyphenyl)piperazin-1-yl]ethyl]thieno[3,4-d]pyrimidine-2,4-dione (1.0 g, 2.6 mmol) in methylene chloride (50 ml) was cooled by an external ice bath and triethylamine (0.393 g, 3.88 mmol) and acetyl chloride (0.305 g, 3.88 mmol) were added. After stirring for 1 hour, the mixture was warmed to room temperature and quenched with water (10 ml). The separated organic layer was washed with water and saturated brine and dried over magnesium sulfate. The solution was concentrated in vacuo, treated with toluene (10 ml) and reconcentrated to give the product (0.93 g, 83.5% yield) which was recrystallized from methylene chloride-hexanes to give the analytical sample as light brown crystals, mp 128°-129° C.

Theor. $C_{21}H_{24}N_4O_4S$: C, 58.86; H, 5.65; N, 13.08. Found: C, 58.78; H, 5.69; N, 13.05.

EXAMPLE 39

3-[2-[4-(2-Methoxyphenyl)piperazin-1-yl]ethyl]-1-(2-methyl-1-oxopropyl)thieno[3,4-d]pyrimidine-2,4-dione When isobutyryl chloride (0.662 g, 6.2 mmol) was used as the acylating agent in the procedure of Example 38, the title compound was isolated as a white crystalline solid (1.4 g, 58.9% yield), mp 129°-130.5° C.

Theor. $C_{23}H_{28}N_4O_4S$: C, 60.50; H, 6.18; N, 12.27. Found: C, 60.58; H, 6.28; N, 11.88.

EXAMPLE 40

3-[2-[4-(2-Methoxyphenyl)piperazin-1-yl]ethyl]-1-(1-oxohexyl)thieno[3,4-d]pyrimidine-2,4-dione When hexanoyl chloride (0.836 g, 6.2 mmol) was used as the acylating agent in the procedure of Example 38, the title compound was obtained as a buff colored solid (1.24 g, 49.2% yield), mp 81°-82.5° C.

Theor. $C_{25}H_{32}N_4O_4S$: C, 61.98; H, 6.66; N, 11.56. Found: C, 61.95; H, 6.84; N, 11.14.

EXAMPLE 41

3-[2-[4-(2-Methoxyphenyl)piperazin-1-yl]ethyl]-1-(2,2-dimethyl-1-oxopropyl)thieno[3,4-d]pyrimidine-2,4-dione When trimethylacetyl chloride (0.749 g, 6.2 mmol) was used as the acylating agent in the procedure of Example 38, the title compound was obtained as a buff colored solid (1.57 g, 64.1% yield), mp 116°-117° C.

Theor. $C_{24}H_{30}N_4O_4S$: C, 61.25; H, 6.49; N, 11.91. Found: C, 61.32; H, 6.49; N, 11.59.

EXAMPLE 42

1-Benzoyl-3-[2-[4-(2-methoxyphenyl)piperazin-1-yl]ethyl]thieno[3,4-d]pyrimidine-2,4-dione When benzoyl chloride (0.873 g, 6.2 mmol) was used as the acylating agent in the procedure of Example 38, the title compound was obtained as a white solid (1.2 g, 47% yield), mp 112°-113.5° C.

Theor. $C_{26}H_{26}N_4O_4S$: C, 63.85; H, 5.34; N, 11.42. Found: C, 63.42; H, 5.47; N, 11.23.

EXAMPLE 43

1-(4-Chlorobenzoyl)-3-[2-[4-(2-methoxyphenyl)piperazin-1-yl]ethyl]thieno[3,4-d]pyrimidine-2,4-dione When 4-chlorobenzoyl chloride (1.08 g, 6.2 mmol) was used as the acylating agent in the procedure of Example 38, the title compound was obtained as a white solid (0.822 g, 30.1% yield), mp 173°–174.5° C.

Theor. $C_{26}H_{25}ClN_4O_4S$: C, 59.48; H, 4.80; N, 10.67. Found: C, 59.13; H, 4.69; N, 10.50.

When in the above procedure, 4-methoxybenzoyl chloride is employed, the corresponding 1-(4-methoxybenzoyl) derivative is obtained.

EXAMPLE 44

Methyl 3-[2-[4-(2-methoxyphenyl)piperazin-1-yl]ethyl]-2,4-dioxothieno[3,4-d]pyrimidine-1-(5-oxopentanoate)

When methyl 4-(chloroformyl)butyrate (1.02 g, 6.2 mmol) was used as the acylating agent in the procedure of Example 38, the title compound was isolated as a white crystalline solid (0.435 g, 16.3% yield), mp 94°–95° C.

Theor. $C_{25}H_{30}N_4O_6S$: C, 58.35; H, 5.88; N, 10.89. Found: C, 58.18; H, 5.92; N, 10.67.

EXAMPLE 45

1-Acetyl-3-[2-[4-(2-methoxyphenyl)piperazin-1-yl]ethyl]thieno[3,2-d]pyrimidine-2,4-dione A solution of 3-[2-[4-(2-methoxyphenyl)piperazin-1-yl]ethyl]thieno[3,2-d]pyrimidine-2,4-dione (2.6 g, 6.73 mmol) in acetic anhydride (30 ml) was heated to reflux for 5 hours. Acetic anhydride was removed in vacuo. The residue was dissolved in toluene, and the toluene was removed in vacuo. This process was repeated twice to remove any residual acetic anhydride. The residue was purified by flash chromatography on silica gel 60 (60 g) using 2.5% methanol in methylene chloride as eluant to give the product (1.65 g, 57% yield) as an off-white solid, mp 156°–158° C.

Theor. $C_{21}H_{24}N_4O_4S$: C, 58.86; H, 5.64; N, 13.07; S, 7.48. Found: C, 58.87; H, 5.75; N, 12.83; S, 7.44.

EXAMPLE 46

3-[2-[4-(2-Methoxyphenyl)piperazin-1-yl]ethyl]-1-(2,2-dimethyl-1-oxopropyl)thieno[3,2-d]pyrimidine-2,4-dione A mixture of 3-[2-[4-(2-methoxyphenyl)piperazin-1-yl]ethyl]thieno[3,2-d]pyrimidine-2,4-dione (3.23 g, 8.36 mmol) and sodium hydride (60% in mineral oil, prewashed with pentane, 435 mg, 10.9 mmol) in N,N-dimethylformamide (50 ml) was allowed to equilibrate for one hour. Trimethylacetyl chloride (1.35 ml, 10.9 mmol) was added to the resultant solution, and stirred at room temperature for 16 hours. The solution was poured into ice water (200 ml) and extracted with methylene chloride (100 ml). The methylene chloride solution was washed with water (4×100 ml) and dried over magnesium sulfate. The solvent was removed in vacuo and the resultant oil was purified by flash chromatography on silica gel 60 (100 g) using 2% methanol in methylene chloride as eluant to give the product (1.56 g, 40% yield) as a beige solid, mp 117°–120° C.

Theor. $C_{24}H_{30}N_4O_4S$: C, 61.26; H, 6.43; N, 11.91; S, 6.91. Found: C, 61.09; H, 6.49; N, 11.90; S, 6.76.

When in the above procedure, benzoyl chloride, 4-methoxybenzoyl chloride or 4-chlorobenzoyl chloride is employed as the acylating agent, the corresponding 2-benzoyl, 1-(4-methoxybenzoyl) or 1-(4-chlorobenzoyl) derivative is obtained.

When in the above procedures, 3-[2-[4-(2-methoxyphenyl)piperazin-1-yl]ethyl]thieno[2,3-d]pyrimidine-2,4-dione is utilized, the corresponding thieno[2,3-d]pyrimidine-2,4-dione derivative is obtained.

EXAMPLE 47

Ethyl 3-[2-[4-(2-methoxyphenyl)piperazin-1-yl]ethyl]-2,4-dioxothieno[3,2-d]pyrimidine-1-carboxylate A mixture of 3-[2-[4-(2-methoxyphenyl)piperazin-1-yl]ethyl]thieno[3,2-d]pyrimidine-2,4-dione (2.62 g, 6.77 mmol) and sodium hydride (60% in mineral oil, prewashed with pentane, 325 mg, 8.13 mmol) in N,N-dimethylformamide (50 ml) was allowed to equilibrate for one hour. Ethyl chloroformate (0.78 ml, 8.13 mmol) was added to the resultant solution, and stirred at room temperature for 16 hours. The solution was poured into ice water (200 ml) and the resultant solid was collected by filtration, washed with water and air dried. The solid was purified by flash chromatography on silica gel 60 (100 g) using 1% methanol in methylene chloride as eluant to give the product (0.88 g, 28% yield) as a colorless solid, mp 121°–122° C.

Theor. $C_{22}H_{26}N_4O_5S$: C, 57.62; H, 5.71; N, 12.21; S, 6.99. Found: C, 53.87; H, 5.78; N, 11.93; S, 6.93.

EXAMPLE 48

Antihypertensive Activity

The antihypertensive activity of the compounds was tested as follows. Adult male spontaneously hypertensive rats (SHR) were placed in restrainers in a chamber warmed to 32° C. A standard indirect method employing a pneumatic pulse transducer and inflatable tail cuff was used to measure systolic blood pressure (SBP) in the conscious state. After baseline SBPs were recorded, groups of 4–6 SHR received a single oral dose of drug or vehicle (0.5% methylcellulose) administered with a gavage tube at doses of 0.5–20 mg/kg. SBPs were obtained at ½, 1, 2, 3 and 4 hours post-treatment. Changes in SBPs were statistically compared to the vehicle effect using Students t test at p=0.05. The results for representative compounds are shown in Table I.

TABLE I

| Antihypertensive Effect of Representative Thienopyrimidine-2,4-dione Derivatives | | |
|---|---|---|
| Compound (Example) | Dose (mg/kg) | Change from Pre-Drug Systolic Blood Pressure (mm Hg) |
| 1 | 0.5 | −83 |
|  | 1.25 | −63 |
|  | 2.50 | −106 |
| 2 | 10 | −70 |
| 3 | 1.25 | −36 |
| 4 | 1.25 | −51 |
| 5 | 10 | −20 |
|  | 20 | −19 |
| 6 | 10 | −51 |
| 7 | 20 | −52 |
| 8 | 10 | −56 |
| 9 | 10 | −68 |
| 10 | 10 | −76 |
| 11 | 10 | −38 |
| 12 | 1.25 | −66 |
|  | 10 | −83 |
| 13 | 1.25 | −67 |
| 14 | 10 | −50 |

TABLE I-continued

Antihypertensive Effect of Representative
Thienopyrimidine-2,4-dione Derivatives

| Compound (Example) | Dose (mg/kg) | Change from Pre-Drug Systolic Blood Pressure (mm Hg) |
|---|---|---|
| 15 | 10 | −52 |
| 16 | 10 | −54 |
| 17 | 10 | −55 |
| 18 | 1.25 | −37 |
|    | 10 | −87 |
| 19 | 1.25 | −74 |
|    | 2.50 | −50 |
| 19 (urea intermediate) | 10 | −35 |
| 20 | 1.25 | −33 |
| 21 | 1.25 | −30 |
| 22 | 10 | −68 |
| 23 | 10 | −48 |
| 24 | 10 | −43 |
| 25 | 1.25 | −56 |
| 26 | 1.25 | −28 |
|    | 10 | −78 |
| 27 | 2.5 | −30 |
| 28 | 1.25 | −50 |
|    | 2.50 | −68 |
| 29 | 1.25 | −19 |
|    | 10 | −70 |
| 30 | 10 | −43 |
| 31 | 10 | −45 |
| 32 | 10 | −40 |
| 33 | 10 | −68 |
| 34 | 10 | −56 |
| 35 | 1.25 | −25 |
|    | 20 | −91 |
| 36 | 1.25 | −23 |
|    | 20 | −50 |
| 37 | 1.25 | −28 |
| 38 | 2.5 | −44 |
| 39 | 5 | −53 |
| 40 | 5 | −42 |
| 41 | 5 | −69 |
| 42 | 5 | −64 |
| 44 | 5 | −46 |
| 45 | 5 | −58 |

EXAMPLE 49

Vasodilatory Activity

The vasodilatory activity of the compounds was tested as follows. Adult mongrel dogs were anesthetized and surgically prepared for electromagnetic measurement of renal artery blood flow. A carotid artery was cannulated for measuring arterial blood pressure and drugs were administered intravenously or intraarterially (renal artery). Heart rate was monitored by a cardiotachometer. Renal vascular resistance (RVR) was calculated as the ratio of mean arterial blood pressure/renal artery blood flow. Dopamine was infused intravenously at 3 μg/kg/min for 10 minutes (1 ml/min) to determine responsiveness of each dog to renal dopamine receptor stimulation. Cumulative dose-response data were obtained by infusing the test drug at progressively increasing (usually three-fold) infusion rates, each dose being infused for five minutes. The maximum percent increase from pre-drug control in renal artery blood flow (RBF) or decrease in renal vascular resistance (RVR) was quantitated for each infusion dose. The results for representative compounds are shown in Table II.

TABLE II

Vasodilatory Effects of Representative Thienopyrimidine-2,4-dione Derivatives in Anesthetized Dog

| Compound (Example) | Total Cumulative Dose (mg/kg i.v.) | Percent Change From Pre-Drug Baseline | |
|---|---|---|---|
|  |  | RBF | RVR |
| 1 | 1.2 | +52 | −46 |
| 2 | 0.2 | +19 | −42 |
| 3 | 6.2 | +46 | −42 |
| 4 | 1.2 | +10 | −18 |
| 19 | 0.24 | +24 | −40 |
| 19 (urea intermediate) | 1.2 | +17 | −54 |
| 23 | 1.2 | +15 | −36 |
| 26 | 1.2 | +20 | −33 |
| 28 | 1.2 | +15 | −21 |
| 41 | 6.2 | +15 | −30 |

What is claimed is:
1. A compound of the formula

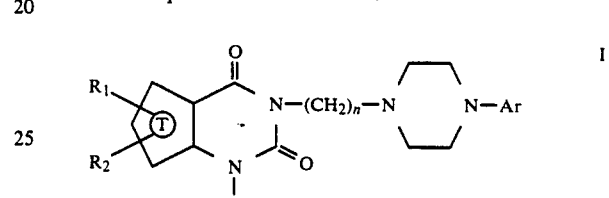

where

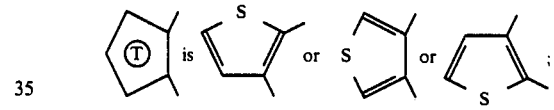

$R_1$ and $R_2$ are the same or different and are hydrogen, F, Cl, Br, nitro, $C_1$–$C_3$ alkyl or $R_1$ and $R_2$ together are —$(CH_2)_4$— when

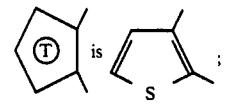

$R_3$ is hydrogen, $C_1$–$C_{10}$ straight or branched-chain alkyl, $C_3$–$C_6$ alkenyl, $C_3$–$C_6$ alkynyl, —$(CH_2)_m$—$CO_2R_5$, —$(CH_2)_m CONR_6R_7$, —$COR_8$ or —$CO_2R_9$;

$R_5$ is hydrogen, $C_1$–$C_3$ alkyl, pharmaceutically acceptable alkali metal ion, pharmaceutically acceptable alkaline earth metal ion or pharmaceutically acceptable quaternary ammonium ion;

$R_6$ and $R_7$ are the same or different and are hydrogen or $C_1$–$C_3$ alkyl;

$R_8$ is $C_1$–$C_5$ straight or branched-chain alkyl, —$(CH_2)_m$—$CO_2R_5$, phenyl or phenyl substituted by F, Cl, Br, $C_1$–$C_2$ alkyl or $C_1$–$C_2$ alkoxy;

$R_9$ is $C_1$–$C_3$ alkyl;

Ar is

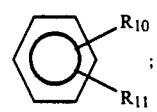

$R_{10}$ and $R_{11}$ are the same or different and are hydrogen, $NO_2$, $CF_3$, F, Cl, Br, $C_1$–$C_3$ alkyl or $C_1$–$C_2$ alkoxy;

m is 2–6; and n is 2–4.

2. A compound of claim 1 wherein $R_3$ is —$COR_8$.

3. A compound of claim 1 wherein $R_3$ is —$CO_2R_9$.

4. A compound of claim 1 wherein $R_3$ is —$(CH_2)_m$—$CO_2R_5$ or —$(CH_2)_m$—$CONR_6R_7$.

5. A compound of claim 1 wherein $R_3$ is hydrogen, $C_1$–$C_{10}$ straight or branched-chain alkyl, $C_3$–$C_6$ alkenyl or $C_3$–$C_6$ alkynyl.

6. A compound of claim 1 selected from the group consisting of 3-[2-[4-(2-methoxyphenyl]piperazin-1-yl]ethyl]thieno[3,4-d]pyrimidine-2,4-dione; 3-[2-[4-(2-methylphenyl)piperazin-1-yl]ethyl]thieno[3,4-d]pyrimidine-2,4-dione; 3-[2-[4-(2-chlorophenyl)piperazin-1-yl]ethyl]thieno[3,4-d]pyrimidine-2,4-dione; 3-[2-[4-(3-chlorophenyl)piperazin-1-yl]ethyl]thieno[3,4-d]pyrimidine-2,4-dione; 3-[2-[4-(4-methoxyphenyl)piperazin-1-yl]ethyl]thieno[3,4-d]pyrimidine-2,4-dione; 3-[2-[4-(3-methoxyphenyl)piperazin-1-yl]ethyl]thieno[3,4-d]pyrimidine-2,4-dione; 3-[2-[4-(4-chlorophenyl)piperazin-1-yl]ethyl]thieno[3,4-d]pyrimidine-2,4-dione; 3-[2-[4-(4-fluorophenyl)piperazin-1-yl]ethyl]thieno[3,4-d]pyrimidine-2,4-dione; 3-[2-(4-phenylpiperazin-1-yl)ethyl]thieno[3,4-d]pyrimidine-2,4-dione; 3-[3-[4-(2-methoxyphenyl)piperazin-1-yl]propyl]thieno[3,4-d]pyrimidine-2,4-dione; and 3-[2-[4-(2-methoxyphenyl)piperazin-1-yl]ethyl]-5-methylthieno[3,4-d]pyrimidine-2,4-dione.

7. A compound of claim 1 selected from the group consisting of 3-[2-[4-(2-methoxyphenyl)piperazin-1-yl]ethyl]thieno[3,2-d]pyrimidine-2,4-dione; 3-[2-[4-(2-methylphenyl)piperazin-1-yl]ethyl]thieno[3,2-d]pyrimidine-2,4-dione; 3-[2-[4-(2-chlorophenyl)piperazin-1-yl]ethyl]thieno[3,2-d]pyrimidine-2,4-dione; 3-[2-[4-(4-methoxyphenyl)piperazin-1-yl]ethyl]thieno[3,2-d]pyrimidine-2,4-dione; 3-[2-(4-phenylpiperazin-1-yl)ethyl]thieno[3,2-d]pyrimidine-2,4-dione; and 3-[3-[4-(2-methoxyphenyl)piperazin-1-yl]propyl]thieno[3,2-d]pyrimidine-2,4-dione.

8. A compound of claim 1 selected from the group consisting of 3-[2-[4-(2-methoxyphenyl)piperazin-1-yl]ethyl]thieno[2,3-d]pyrimidine-2,4-dione; 3-[2-[4-(2-methylphenyl)piperazin-1-yl]ethyl]thieno[2,3-d]pyrimidine-2,4-dione; 3-[2-[4-(2-chlorophenyl)piperazin-1-yl]ethyl]thieno[2,3-d]pyrimidine-2,4-dione; 3-[2-(4-phenylpiperazin-1-yl)ethyl]thieno[2,3-d]pyrimidine-2,4-dione; 3-[2-[4-(4-methoxyphenyl)piperazin-1-yl]ethyl]thieno[2,3-d]pyrimidine-2,4-dione; 3-[3-[4-(2-methoxyphenyl)piperazin-1-yl]propyl]thieno[2,3-d]pyrimidine-2,4-dione; 3-[2-[4-(2-methoxyphenyl)piperazin-1-yl]ethyl]-5-methylthieno[2,3-d]pyrimidine-2,4-dione; 6-chloro-3-[2-[4-(2-methoxyphenyl)piperazin-1-yl]ethyl]thieno[2,3-d]pyrimidine-2,4-dione; and 3-[2-[4-(2-methoxyphenyl)piperazin-1-yl]ethyl]-5,6-dimethylthieno[2,3-d]pyrimidine-2,4-dione.

9. A compound of claim 1 selected from the group consisting of 3-[2-[4-(2-methoxyphenyl)piperazin-1-yl]ethyl]-1-methylthieno[3,4-d]pyrimidine-2,4-dione; 3-[2-[4-(2-methoxyphenyl)piperazin-1-yl]ethyl]-1-(propen-3-yl)thieno[3,4-d]pyrimidine-2,4-dione; 3-[2-[4-(2-methoxyphenyl)piperazin-1-yl]ethyl]-1-(propyn-3-yl)thieno[3,4-d]pyrimidine-2,4-dione; 3-[2-[4-(2-methoxyphenyl)piperazin-1-yl]ethyl]-1-(octyl)thieno[3,4-d]pyrimidine-2,4-dione; 3-[2-[4-(2-methoxyphenyl)piperazin-1-yl]ethyl]-1-methylthieno[3,2-d]pyrimidine-2,4-dione; 1-(butyl)-3-[2-[4-(2-methoxyphenyl)piperazin-1-yl]ethyl]thieno[3,2-d]pyrimidine-2,4-dione; and 3-[2-[4-(2-methoxyphenyl)piperazin-1-yl]ethyl]-1-methylthieno[2,3-d]pyrimidine-2,4-dione.

10. A compound of claim 1 selected from the group consisting of 1-(2-methoxycarbonyl)ethyl-3-[2-[4-(2-methoxyphenyl)piperazin-1-yl]ethyl]thieno[3,4-d]pyrimidine-2,4-dione; 1-[3-(ethoxycarbonyl)propyl]-3-[2-[4-(2-methoxyphenyl)piperazin-1-yl]ethyl]-thieno[3,4-d]pyrimidine-2,4-dione; and 1-[4-(ethoxycarbonyl)butyl]-3-[2-[4-(2-methoxyphenyl)piperazin-1-yl]ethyl]thieno[3,2-d]pyrimidine-2,4-dione.

11. A compound of claim 1 which is ethyl 3-[2-[4-(2-methoxyphenyl)piperazin-1-yl]ethyl]-2,4-dioxothieno[3,2-d]pyrimidine-1-carboxylate.

12. A compound of claim 1 selected from the group consisting of 1-acetyl-3-[2-[4-(2-methoxyphenyl)piperazin-1-yl]ethyl]thieno[3,4-d]pyrimidine-2,4-dione; 3-[2-[4-(2-methoxyphenyl)piperazin-1-yl]ethyl]-1-(2-methyl-1-oxopropyl)thieno[3,4-d]pyrimidine-2,4-dione; 3-[2-[4-(2-methoxyphenyl)piperazin-1-yl]ethyl]-1-(1-oxohexyl)thieno[3,4-d]pyrimidine-2,4-dione; 3-[2-[4-(2-methoxyphenyl)piperazin-1-yl]ethyl]-1-(2,2-dimethyl-1-oxopropyl)thieno[3,4-d]pyrimidine-2,4-dione; 1-benzoyl-3-[2-[4-(2-methoxyphenyl)piperazin-1-yl]ethyl]thieno[3,4-d]pyrimidine-2,4-dione; 1-(4-chlorobenzoyl)-3-[2-[4-(2-methoxyphenyl)piperazin-1-yl]ethyl]thieno[3,4-d]pyrimidine-2,4-dione; methyl 3-[2-[4-(2-methoxyphenyl)piperazin-1-yl]ethyl]-2,4-dioxothieno[3,4-d]pyrimidine-1-(5-oxopentanoate); 1-acetyl-3-[2-[4-(2-methoxyphenyl)piperazin-1-yl]ethyl]thieno[3,2-d]pyrimidine-2,4-dione; and 3-[2-[4-(2-methoxyphenyl)piperazin-1-yl]ethyl]-1-(2,2-dimethyl-1-oxopropyl)thieno[3,2-d]pyrimidine-2,4-dione.

* * * * *